United States Patent
Togawa et al.

(10) Patent No.: US 7,744,820 B2
(45) Date of Patent: Jun. 29, 2010

(54) PLASMA OR SERUM SEPARATION MEMBRANE AND FILTER APPARATUS INCLUDING THE PLASMA OR SERUM SEPARATION MEMBRANE

(76) Inventors: Katsuya Togawa, c/o Sekisui Chemical Co., Ltd., 4560, Kaiseicho, Shunan-city, Yamaguchi 746-0006 (JP); Ryusuke Okamoto, c/o Sekisui Chemical Co., Ltd., 4560, Kaiseicho, Shunan-city, Yamaguchi 746-0006 (JP); Hironobu Isogawa, c/o Sekisui Chemical Co., Ltd., Toranomon 2-chome Tower, 2-3-17, Toranomon, Minato-ku, Tokyo 105-8450 (JP)

( * ) Notice: Subject to any disclaimer, the term of this patent is extended or adjusted under 35 U.S.C. 154(b) by 244 days.

(21) Appl. No.: 11/635,239

(22) Filed: Dec. 7, 2006

(65) Prior Publication Data

US 2007/0082370 A1  Apr. 12, 2007

Related U.S. Application Data

(62) Division of application No. 10/533,539, filed on May 2, 2005.

(51) Int. Cl.
- B01L 11/00 (2006.01)
- G01N 15/06 (2006.01)
- C12M 1/36 (2006.01)
- C12M 1/34 (2006.01)
- G01N 1/00 (2006.01)
- G01N 1/18 (2006.01)
- B01D 33/00 (2006.01)
- B01D 63/00 (2006.01)

(52) U.S. Cl. .............. 422/101; 422/68.1; 435/286.1; 435/286.5; 435/287.1; 435/287.7; 436/174; 436/175; 436/177; 436/178; 210/348; 210/500.21

(58) Field of Classification Search ............... 422/68.1, 422/101; 435/286.1, 286.5, 287.1, 287.7; 436/174, 175, 177, 178; 210/348, 500.21
See application file for complete search history.

(56) References Cited

U.S. PATENT DOCUMENTS 3,607,093 A * 9/1971 Stone .................. 422/56

(Continued)

FOREIGN PATENT DOCUMENTS

JP  56-135525 A  10/1981

(Continued)

OTHER PUBLICATIONS

English translation of the Office Action issued on Feb. 2, 2007, in the counterpart Chinese application.

(Continued)

*Primary Examiner*—Bao-Thuy L Nguyen
*Assistant Examiner*—Jacqueline Diramio
(74) *Attorney, Agent, or Firm*—Townsend & Banta

(57) ABSTRACT

A Plasma or serum separation membrane that enables omitting centrifugal separation, is free from hemolysis attributed to destruction of red blood cells and realizes easy and rapid separation of plasma or serum from blood; and a filter apparatus including the plasma or serum separation membrane. In particular, a plasma or serum separation membrane being a membrane for separation of plasma or serum from blood and having a void ratio of 30% or below; and a filter apparatus comprising a filter member capable of attaining movement of plasma swifter than movement of blood cells and a plasma or serum separation membrane connected in series with a rear side of the filter member.

1 Claim, 11 Drawing Sheets

U.S. PATENT DOCUMENTS

| | | | | |
|---|---|---|---|---|
| 5,998,214 A | * | 12/1999 | Guirguis | 436/165 |
| 2003/0089660 A1 | * | 5/2003 | Huang et al. | 210/500.36 |
| 2004/0219073 A1 | * | 11/2004 | Radcliffe et al. | 422/101 |

FOREIGN PATENT DOCUMENTS

| | | |
|---|---|---|
| JP | 10-211277 A | 11/1988 |
| JP | 02-174851 A | 7/1990 |
| JP | 6-64054 A | 8/1994 |
| JP | 09-196911 A | 7/1997 |
| JP | 10-57786 A | 3/1998 |
| JP | 2000-180444 A | 6/2000 |
| JP | 2003-287532 A | 10/2003 |
| WO | WO 99/51316 | 10/1999 |

OTHER PUBLICATIONS

Office Action issued on Jul. 4, 2007, in corresponding Japanese Application 2003-388441, no translation.

* cited by examiner

PLASMA OR SERUM SEPARATION MEMBRANE AND FILTER APPARATUS INCLUDING THE PLASMA OR SERUM SEPARATION MEMBRANE

This is a divisional application of U.S. patent application Ser. No. 10/553,539, filed May 2, 2005.

FIELD OF THE INVENTION

The present invention relates to plasma or serum separating membranes for use in separation of plasma or serum components in blood containing corpuscles, and more specifically, to a plasma or serum separating membrane and a filter apparatus enabling separation of plasma or serum components without causing breakage of erythrocytes.

BACKGROUND ART

Conventionally, a variety of separating membranes have been proposed for removing corpuscles from blood to obtain plasma or serum required for laboratory tests.

For example, Japanese Examined Patent Publication No. 2-23831 (1990) discloses a method of colleting plasma from blood using a hollow fiber having fine pores of 0.05 to 1 μm in diameter, a porosity of outer surface of not more than 40%, and a porosity of inner surface of not less than 60%.

Japanese Examined Patent publication No. 6-64054 (1994) proposes a method of separating plasma or serum through a fiber layer having a mean diameter of 0.2 to 5.0 μm and a density of 0.1 to 0.5 g/cm$^3$.

On the other hand, Japanese Unexamined Patent Publication No. 11-285607 (1999) discloses a separation method which utilizes difference in movement speed between corpuscles and plasma or serum components through a polymeric microfiber assembly or a porous polymer. In this method, a hydrophilic polymer is immobilized on a surface of fiber, the hydrophilic polymer swells after separation of plasma or serum, the filter is clogged, and thereby filtration is automatically stopped.

However, the method disclosed in Japanese Examined Patent Publication No. 2-23831 (1990) had an economic problem because high cost is required to produce a disposable product due to the hollow fiber.

The method of Japanese Examined Patent Publication No. 6-64054 enables separation of plasma or serum, however the filtering speed is still unsatisfactory. Application of pressure to improve the filtering speed could sometimes cause breakage of corpuscles, hemolysis, and contamination of separated plasma or serum with leaking erythrocytes. Additionally, in the blood in which fibrin or the like precipitates, hemolysis was more likely to occur since clogging was more likely to occur during the separation process.

In the method of Japanese Unexamined Patent Publication JP-A 11-285607 (1999), since the filtering speed changes between bloods of different hematocrits and viscosities, it was impossible to securely stop the filtration at the point when filtration of plasma or serum completed.

DISCLOSURE OF THE INVENTION

In consideration of the above circumstances of the conventional arts, it is an object of the present invention to provide a plasma or serum separating membrane enabling reliable and rapid separation of plasma or serum components from blood without causing breakage of erythrocytes, and to provide a filter apparatus using the plasma or serum separating membrane.

As a result of diligent research for separation of plasma or serum components from corpuscles in blood, the inventors of the present application found that plasma or serum components can be separated from corpuscles without causing hemolysis by using a separation membrane having pores of specific constitution and accomplished the present invention.

A plasma or serum separating membrane of the present invention is intended to separate plasma or serum from blood, and is characterized by having a porosity of not more than 30%.

In another specific aspect of the plasma or serum separating membrane of the present invention, a plurality of through holes are provided so as to penetrate from one side to the other side of the membrane.

In a more specific aspect of the present invention, diameters of the through holes fall within the range of 0.05 to 2.0 μm.

In still another specific aspect of the plasma or serum separating membrane of the present invention, mean surface roughness of the membrane is not more than 100 nm.

In a further specific aspect of the plasma or serum separating membrane of the present invention, the plasma or serum separating membrane is used as a corpuscle blocking membrane for preventing contamination by corpuscles.

A filter apparatus of the present invention comprises a first filter member through which plasma can move faster than corpuscles, and a plasma or serum separating membrane according to the present invention, serially connected in subsequent stage with the first filter member.

In this description, the expression "serially connected" refers to not only the case where the objects are directly connected but also the case where other member intervenes the objects.

In a specific aspect of the filter apparatus of the present invention, the filter member serves as a first filter member, the plasma or serum separating membrane serves as a second filter member, and a third filter member made of fiber having a mean fiber diameter of not less than 3.0 μm and a bulk density of not more than 0.3 g/cm$^3$ is provided in precedent stage of the first filter member.

In another specific aspect of the filter apparatus of the present invention, the first filter member is made of fiber, and mean fiber diameter is from 0.2 to 3.0 μm and filled density is from 0.1 to 0.5 g/cm$^3$.

A filter apparatus in another broader aspect of the present invention comprises a container body having an opening at its one end, a cylindrical member attached to the opening of the container body in liquid-tight manner, a first filter member placed in the cylindrical member, through which plasma can move faster than corpuscles, and a second filter member comprising the membrane for separating plasma or serum from blood according to the present invention, serially connected with the first filter member in subsequent stage in the cylindrical member, and the first and the second filter members are disposed in a filter accommodation part, a blood accommodation part is formed in precedent stage of the filter accommodation part, and a plasma or serum storage part is formed on the downstream side of the filter accommodation part.

In a still another specific aspect of the present invention, the filter apparatus further comprises a third filter member provided in precedent stage of the first filter member, made of fiber having a mean fiber diameter of not less than 3.0 μm and a bulk density of not more than 0.3 g/cm$^3$.

In a further specific aspect of the filter apparatus of the present invention, the first filter member through which plasma can move faster than corpuscles has a property of adsorbing fibrinogen contained in blood, plasma or a fibrinogen solution.

In a further specific aspect of the filter apparatus of the present invention, an anticoagulant component is stored in at least a part-of the internal space of the filter apparatus.

In a further specific aspect of the filter apparatus of the present invention, an accelerator for accelerating coagulation of blood is stored in at least a part of the internal space.

In a further specific aspect of the filter apparatus of the present invention, an aqueous solution having an osmotic pressure of 200 to 300 mOsm/kg is added to at least a part of the section from the blood accommodation part to the first and the second filter members. Preferably, the aqueous solution contains an internal standard substance.

In a further aspect of the filter apparatus of the present invention, a volume ratio of the blood accommodation part, filter accommodation part and plasma or serum storage part is in the range of 0.5-2:1:1-10.

In a further specific aspect of a blood testing container including the filter apparatus according to the present invention, a strip of immunochromatographical diagnostic agent to be added to the separated plasma or serum is stored in the blood testing container.

BEST MODE FOR CARRYING OUT THE INVENTION

Figure 1:
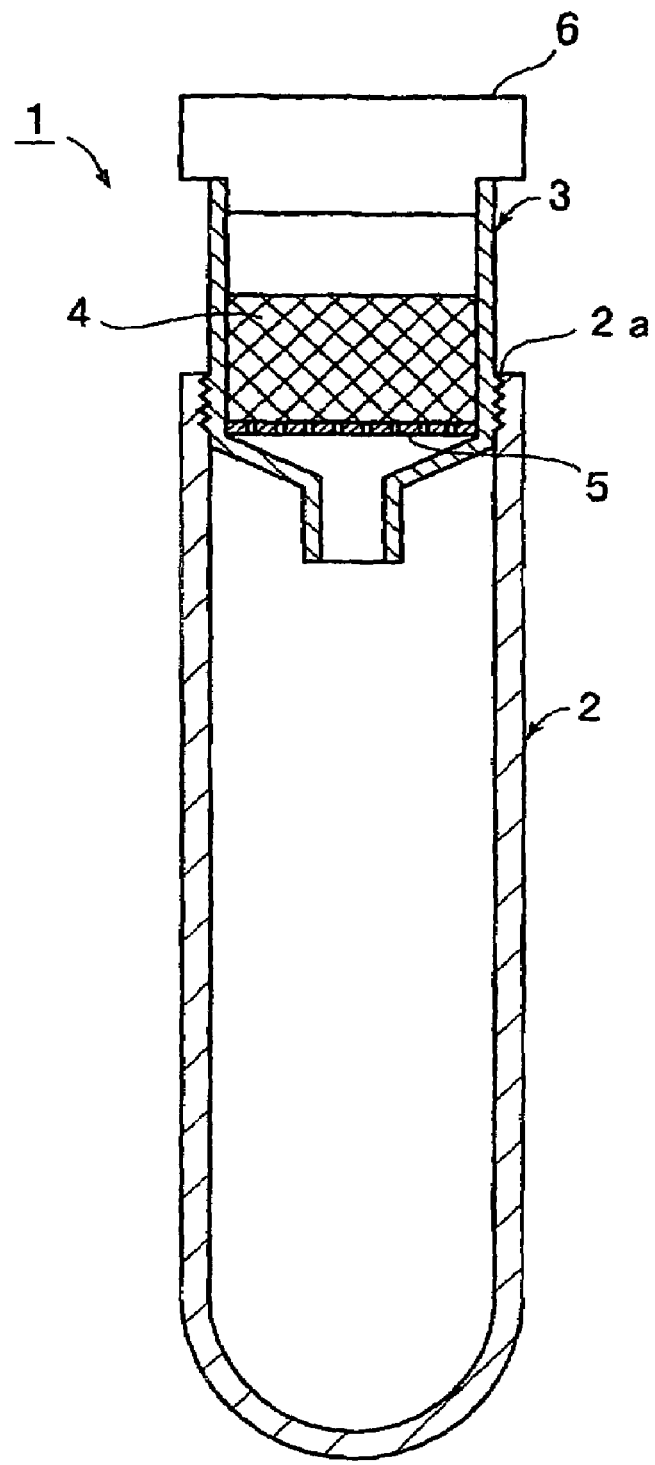
FIG. 1 is a longitudinal section view showing one structural example of a filter apparatus of the present invention.

The present invention will be now described in more detail.

The plasma or serum separating membrane according to the present invention has a porosity of not more than 30%, preferably not more than 25%. If the porosity is more than 30%, the load applied on erythrocytes becomes large, and hemolysis is more likely to occur.

The plasma or serum separating membrane used in the present invention is featured by having a plurality of through holes penetrating from one side to the other side of the membrane. Although the planar shape of opening and the transverse section shape of the through holes are not particularly limited, shapes having acute angels are unfavorable. Therefore, preferably, the planer shape of opening and the transverse section shape of the through holes are curved shapes such as circle or ellipse.

Also the longitudinal section shape along the extending direction of the through holes is not particularly limited, and inside wall may be linear or curve in the longitudinal section. Furthermore, the direction in which the through holes extend may be orthogonal to the surface of the membrane or may be inclined from the orthogonal direction. The through holes may have a longitudinal section of cut truncated cone.

As a method for forming the aforementioned through holes, irradiation with energy beams such as ion beam irradiation or chemical treatments such as alkaline erosion following the membrane formation can be exemplified without limited thereto. In other words, in the plasma or serum separating membrane according to the present invention, through holes that penetrate from one side to the other side are formed by appropriate means as described above after formation of the membrane.

The through holes preferably have diameters in the range of 0.05 to 2.0 μm. If the diameter is less than 0.05 μm, proteins, lipids and the like in the blood are likely to clog, while if the diameter is more than 2.0 μm, erythrocytes can pass through the membrane due to their deformability. More preferably, the diameter is in the range of 0.1 to 1.5 μm.

Preferably, in the above plasma or serum separating membrane, mean surface roughness of the membrane is not more than 100 nm. If the mean surface roughness exceeds 100 nm, the load applied on erythrocytes becomes large, and hemolysis is more likely to occur.

The aforementioned plasma or serum separating membrane may be made of materials including, but not limited to synthetic polymers or naturally polymers. Examples of such materials include cellulose mixed esters, polyvinylidene difluoride, polytetrafluoroethylene, polycarbonate, polypropylene, polyester, nylon, glass and alumina.

The blood to be subjected to the separating operation in the present invention may be whole blood or a diluted blood sample. The blood is not limited to human blood but may be animal blood. Also the blood may be fresh blood or bloods added with anticoagulants such as heparin, ethylenediamine tetraacetate or citric acid.

In separation of plasma or serum from corpuscles in blood using the aforementioned plasma or serum separating membrane, the blood is supplied to one side of the membrane and the separation is accomplished by filtration. The direction of blood flow and the direction of filtration in this filtration can be arbitrarily selected. In the case of separating plasma or serum from corpuscles in whole blood, it is preferred that the direction of blood flow and the direction of filtration differ from each other, and it is more preferred that these directions are orthogonal to each other. By employing different directions, it is possible to improve the separation efficiency.

In the case where the direction of blood flow and the direction of filtration are identical, clogging sometimes occurs in through holes. However, in the case of separating corpuscles in diluted blood, since clogging is not likely to occur, reliable separation is ensured without causing any clogging even when the direction of blood flow and the direction of filtration are selected to be identical. That is, the plasma or serum separating membrane according to the present invention also serves as a corpuscle blocking membrane.

In the above separating operation, filtration ends upon clogging by erythrocytes. In this case, hemolysis is liable to occur if an excess pressure is applied. In a separating membrane having conventional pores, hemolysis will occur upon application of only a small pressure; whereas in the case of using the plasma or serum separating membrane according to the present invention, hemolysis is unlikely to occur even when a larger pressure is applied. That is, hemolysis is unlikely to occur even when a pressure of 60 kPa or less is applied for filtration. This is attributable to the fact that damages on erythrocytes are reduced because the shape of the plasma or serum separating membrane is a through hole, and preferably the porosity is not more than 30% and the surface of membrane is smooth.

If a pressure larger than 60 kPa is applied, erythrocytes may be gradually broken. Therefore, the pressure to be applied is preferably not more than 60 kPa. The plasma or serum thus obtained can be used to obtain accurate test values.

In a filter apparatus according to the present invention, a first filter member through which plasma can move faster than corpuscles is serially connected to the above plasma or serum separating membrane so that the first filter member is located at a precedent stage of the membrane. When uncoagulated blood is supplied, the blood first passes through the first filter member. At this time, plasma rapidly moves toward the plasma or serum separating membrane, and passes through the plasma or serum separating membrane according to the present invention. In this manner, it is possible to efficiently separate plasma from corpuscles. In this filter apparatus, the filtration ends when erythrocytes clog the through holes of the plasma or serum separating membrane after filtration of plasma.

As to the first filter member through which plasma can move faster than corpuscles, for example, synthetic polymers having fine fiber diameter, fibers made of glass or porous polymers can be used without being particularly limited thereto. When the first filter member is made of a material that adsorbs components to be measured in the blood, the material is preferably subjected to surface treatment. As an agent for surface treatment, polyether-based or silicone-based lubricants, hydrophilic polymers such as polyvinylalcohol and polyvinylpyrrolidone or natural hydrophilic polymers, or polymeric surfactants can be used without being particularly limited thereto.

In the case where the first filter member is made of a synthetic polymer or fiber made of glass, the mean fiber diameter is preferably in the range of 0.2 to 3.0 µm. If the mean fiber diameter is less than 0.2 µm, hemolysis is more likely to occur. On the other hand, if the mean fiber diameter is more than 3.0 µm, the fiber should be packed at high density so as to separate plasma or serum from corpuscles. As a result, the amount of filter member increases as does cost. More preferably, the fiber diameter is in the range of 0.5 to 2.5 µm.

The first filter member may consist of two or more stages insofar as the fiber diameter of 0.2 to 3.0 µm and the packing density of 0.1 to 0.5 g/cm are satisfied. In such a case, it is preferred that the packing density of downstream stage is higher than that of the upstream stage or the packing density of the downstream stage is higher than that of the upstream stage. As a result, it is possible to further increase the separation efficiency of plasma or serum.

In the present invention, preferably, the aforementioned first filter member through which plasma can move faster than corpuscles has a fibrinogen adsorbing ability. The fibrinogen adsorbing filter can be made of, but not particularly limited to, the materials as follows. Polyester-based resins such as polyethyleneterephthalate and polybutyleneterephthalate; nylon resins; polyurethane resins; polystyrene-based resins; resins composed of homopolymers or copolymers of poly(methacrylic acid) ester such as poly(methyl methacrylate); and resins composed of copolymers of polyethylene and vinyl acetate or methacrylic acid ester. These resins may be used in combination of plural kinds. Among others, polyester-based resins are desirably used because they are superior in fibrinogen adsorbing ability and balance of influence on test value.

Since a specimen obtained after removing fibrinogen by adsorption can be handled in the same manner as for serum, versatility for a variety of clinical test is improved. Additionally, since such a specimen will not coagulate even if it is left for a certain time, it can be applied to an automated analyzer without anxiety. For example, the filter apparatus of the present invention may be configured in a blood collection tube, and in such a case, the blood having been collected is directly separated by depressurizing the internal space of the blood collection tube to obtain plasma or serum required for measurement.

Figure 2:
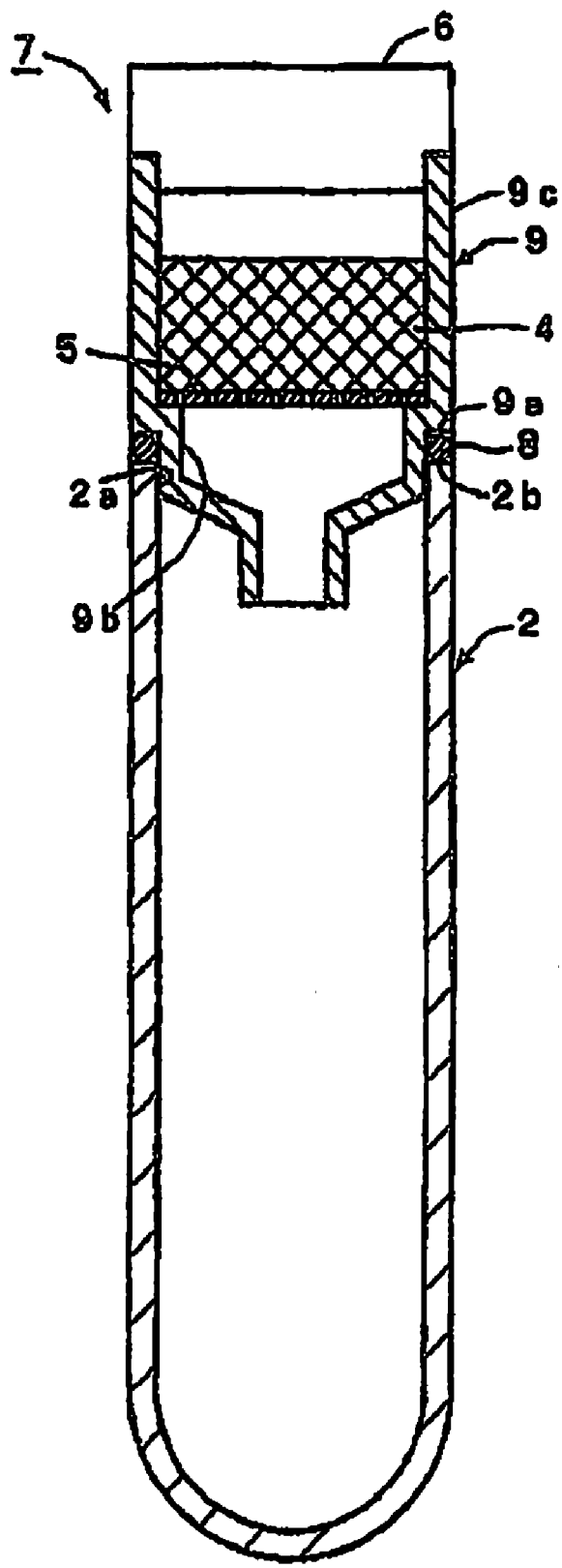
FIG. 2 is a longitudinal section view showing another structural example of a filter apparatus of the present invention.
Figure 3:
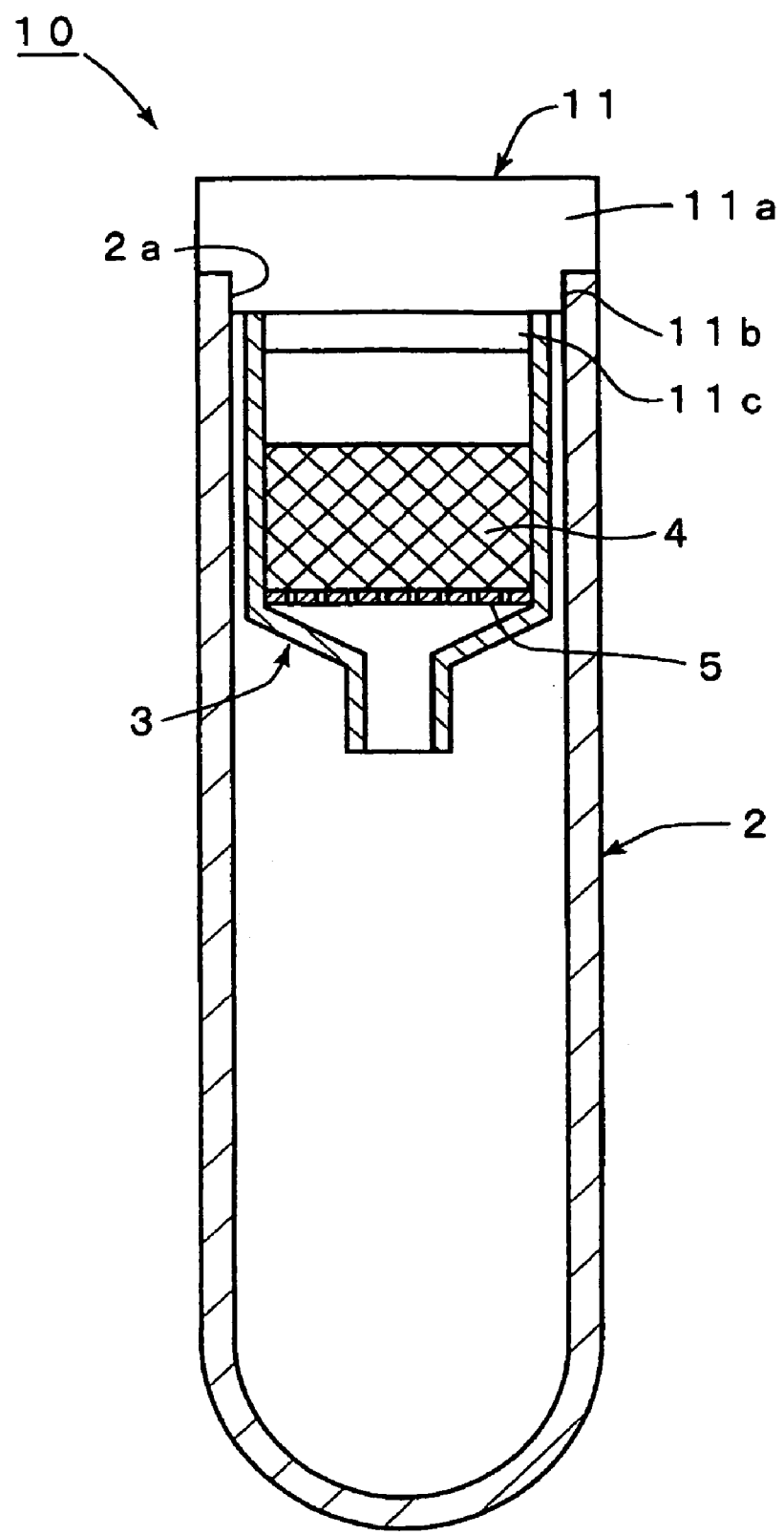
FIG. 3 is a longitudinal section view showing still another structural example of a filter apparatus of the present invention.

In one specific aspect of a filter apparatus according to the present invention, the filter apparatus comprises a container body having an opening at its one end, a cylindrical member attached to the opening of the container body in liquid-tight manner, and in the cylindrical member a first filter member, through which plasma can move faster than corpuscles, and a second filter member comprising the aforementioned membrane for separating plasma or serum from blood, serially connected with the first filter member in subsequent stage in the cylindrical member are disposed. One example of such a filter apparatus is shown in FIGS. 1 to 3.

A filter apparatus 1 shown in FIG. 1 has a container body 2 having an opening 2a at its upper end, and a cylindrical member 3 hermetically inserted into the opening 2a of the container body 2. The container body can be implemented by a blood collection tube, a test tube and the like. And as a material forming the container body 2, synthetic resins, glass and the like can be appropriately used. The cylindrical member 3 can also be formed of appropriate materials such as synthetic resins and plastics. On the outer periphery of a lower end of the cylindrical member 3 is formed a male screw, while on the inner periphery near the opening of the container body 2 is formed a female screw. The cylindrical member 3 is pushed and fixed into the container body 2 by means of these male and female screws. By designing the screwing part between the male screw and the female screw to be hermetically sealed, the outer periphery of the cylindrical member 3 is hermetically fixed to the inner periphery of the container body 2.

In the cylindrical member 3, a filter member 4 is accommodated in an upper part, and a plasma or serum separating membrane 5 is disposed under the filter member 4, namely disposed subsequent and serially to the filter member 4. The outer peripheral edge of the plasma or serum separating membrane 5 is in close contact with the inner peripheral edge of the cylindrical member 3. Above the A filter member 4, a plug member 6 is attached to the opening of the upper end of the cylindrical member 3. This provides hermetical sealing of the opening of the upper end of the cylindrical member 3.

By depressurizing the internal space of the container body 2, the blood collected in the cylindrical member 3 is filtered, and thereby plasma or serum can be separated from corpuscles in accordance with the present invention.

In a filter apparatus 7 illustrated in FIG. 2, a cylindrical member 9 is hermetically fixed to the container body 2 by means of a ring-shaped sealing member 8 having rubber elasticity. In the cylindrical member 9, a smaller diameter portion 9b is connected via a step 9a at a lower position than the part where the filter member 4 and the plasma or serum separating membrane 5 are inserted. The step 9a is opposite to the upper end 2b of the container body 2, and the ring-shaped sealing member 8 implemented by an O-ring, for example is disposed between the step 9a and the upper end 2b. The diameter of the smaller diameter portion 9b of the cylindrical member 9 is dimensioned to be pressed into the opening 2a of the container body 2. Therefore, it is possible to hermetically fix the outer periphery of the cylindrical member 9 against the inner periphery of the container body 2 by pressing the cylindrical member 9 into the container body 2 and compressing the ring-shaped sealing member 8 between the step 9a and the upper end 2b of the container body 2. In a larger diameter portion 9c having a larger diameter than the smaller diameter portion 9b of the cylindrical member 9, the filter member 4 and the plasma or serum separating membrane 5 are disposed. The upper end of the cylindrical member 9 is closely plugged with the plug member 6.

In a filter apparatus 10 illustrated in FIG. 3, the cylindrical member 3 is inserted into the container body 2 and hermetically fixed to the container body 2 by a plug member 11. Concretely, the plug member 11 has a gripping portion 11a and an intermediate portion 11b having a smaller diameter than the gripping portion 11a, and a reduced diameter portion 11c having a diameter which is smaller than that of the intermediate portion 11b. The plug member 11 is made of a material having rubber elasticity such as synthetic rubber or natural rubber. The diameter of the reduced diameter portion 11c has such a diameter that can be pressed into the opening of the upper end of the cylindrical member 3. The intermediate portion 11b has a such a diameter that can be pressed into the container body 2. The gripping portion 11a is dimensioned to have a larger diameter than the outside diameter of the container body 2.

Consequently, as shown in FIG. 3, by pressing the reduced smaller-diameter portion 11c into the cylindrical member 3, and pressing the intermediate portion 11b into the container body 2 via the opening 2a of the container body 2, the cylindrical member 3 is fixedly disposed in the container body 2.

As is apparent from the filter apparatuses 1, 7 and 10 illustrated in FIGS. 1 to 3, a filter apparatus according to the present invention can be structured in various fashions. It is to be noted that the shapes of the container body, cylindrical member and the like are not limited to those shown in the drawings.

In a filter apparatus according to the present invention, preferably, the aforementioned first filter member through which plasma or serum can move faster than corpuscles and a second filter member formed of a plasma or serum separating membrane are serially connected, and on upstream side of the first filter member is provided a third filter member having mean fiber diameter of not less than 3.0 μm and bulk density of not more than 0.3 g/cm$^3$.

The this filter is not particularly limited insofar as it has mean fiber diameter of not less than 3.0 μm and bulk density of not more than 0.3 g/cm$^3$. It is requested that the mean fiber diameter is not less than 3.0 μm and the bulk density is not more than 0.3 g/cm$^3$, however, the mean fiber diameter is desirably not more than 20 μm. If the mean fiber diameter is more than 20 μm, a trace of fibrin and the like that precipitates in the blood can no longer be captured. If the mean fiber diameter is less than 3.0 μm, hemolysis becomes more likely to occur. If the bulk density is more than 0.3 g/cm$^3$, clogging is more likely to occur.

In the case where the aforementioned first to third filter members are provided, the first filter member and the second filter member are serially connected so that the second filter member is on the downstream side, and the third filter member is disposed on the upstream side of the first filter member.

Therefore, in separating plasma or serum from corpuscles in blood, blood is supplied on the third filter member. The blood supplied on the third filter member passes through the third filter member and the first filter member sequentially. In this case, even when thick blood or blood from which fibrin is easy to precipitate is supplied, fibrin and so on are captured by the third filter member to reduce the occurrence of clogging in the first filter member. Therefore, in the first filter member, erythrocytes are not likely to receive excess pressure, so that occurrence of hemolysis can be reduced. In the first filter member, plasma or serum moves faster than corpuscles. Accordingly, plasma or serum passes through the second filter member and separated from the blood. The corpuscles having passed through the first filter member are captured by the second filter member and will not leak downstream the second filter member.

As described above, in the structure that the first and the second filter members are serially connected, since the third filter member is disposed on the upstream side of the first filter member, it is possible to securely separate plasma or serum from blood while suppressing breakage of erythrocytes in the blood separating filter according to the present invention.

The filter apparatus according to the present invention is featured by accommodating the aforementioned blood separating filter of the present invention. Concrete structure for accommodating the blood separating filter is not particularly limited.

Figure 4:
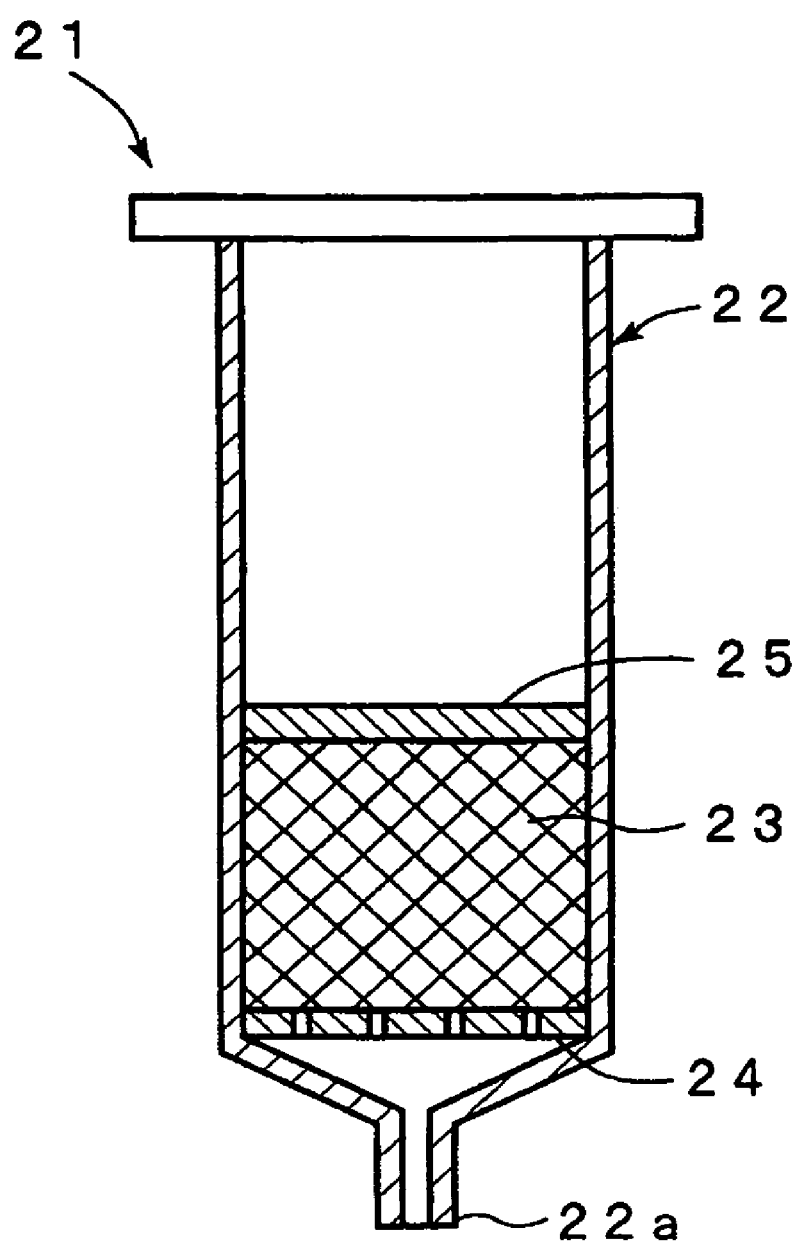
FIG. 4 is a schematic front section view of a filter apparatus in which a blood separation filter according to another embodiment of the present invention is accommodated.

FIG. 4 is a schematic front section view of a filter apparatus according to another embodiment of the present invention. A filter apparatus 21 is formed by using a syringe 22 for injection. In the syringe 22, a first filter member 23 and a second filter member 24 are disposed so that the second filter member 24 is on the downstream side. On the first filter member 23 is disposed a third filter member 25.

Figure 5:
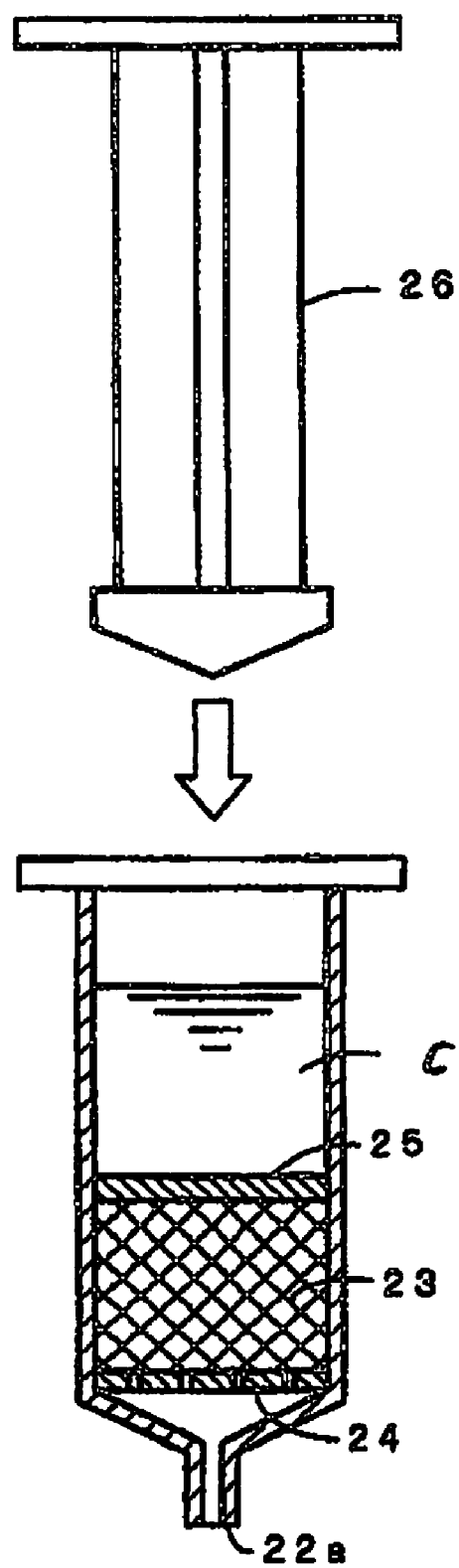
FIG. 5 is a schematic front section view for explaining the process of separating plasma or serum in the filter apparatus shown in FIG. 4.

As illustrated in FIG. 5, in use of the filter apparatus 21, blood is supplied from above the syringe 22, and a piston 26 of the syringe is pushed in. This applies pressure on the blood and separated plasma or serum can be collected on the side of a tip end 22a of the syringe.

Alternative to the procedure of using the piston 26, plasma or serum can be separated by suctioning from the side of the tip end 22a of the syringe 22. For example, by attaching an injection needle to the tip end of the syringe 22 and piercing a plug member of a vacuum blood collection tube (not shown) with the injection needle, plasma or serum is collected in a first internal space A, and can be suctioned from the side of the tip end of the syringe and collected in the vacuum blood collection tube.

Figure 6:
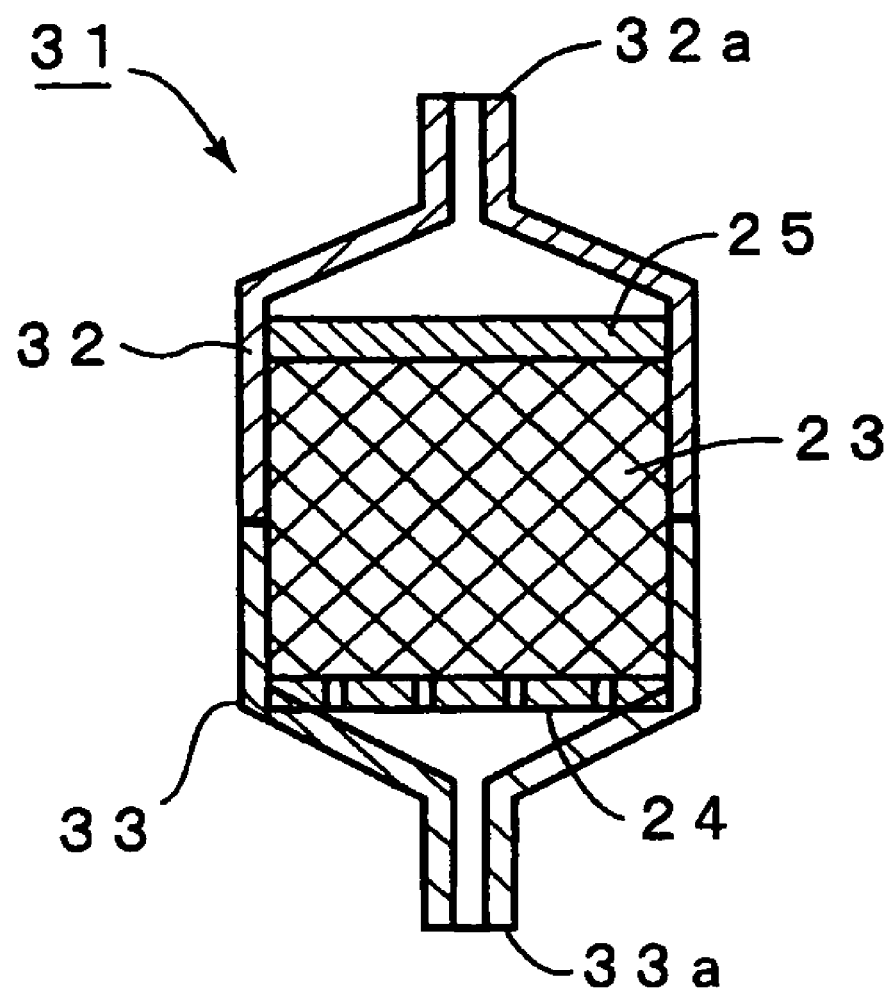
FIG. 6 is a schematic front section view showing a filter apparatus according to still another embodiment of the present invention.

FIG. 6 is a front section view of a filter apparatus in still another embodiment of the present invention. A filter apparatus 31 has a cartridge made up of a case 32 and a case 33. The cases 32 and 33 are detachably fastened by screwing or the like in a liquid-tight manner. In the filter apparatus 31, the first filter member 23, the second filter member 24 and the third filter member 25 are disposed in a similar manner as in the embodiment illustrated in FIG. 4. The filter apparatus 31 has an inlet port 32a through which blood is supplied and an outlet port 33a through which separated plasma or serum is discharged.

In use of this filter apparatus, the inlet port 32a is connected with a syringe and the blood collected by the syringe is pushed by a piston, whereby plasma or serum is separated from the blood by means of the first to the third filter members 23 to 25 and collected via the outlet port 33a. Also in the filter apparatus 31, plasma or serum may be separated by suctioning from the side of the outlet port 33a.

The cases 32, 33 constituting the aforementioned filter apparatus 31 may be realized by a commercially available filter cartridge.

Figure 7:
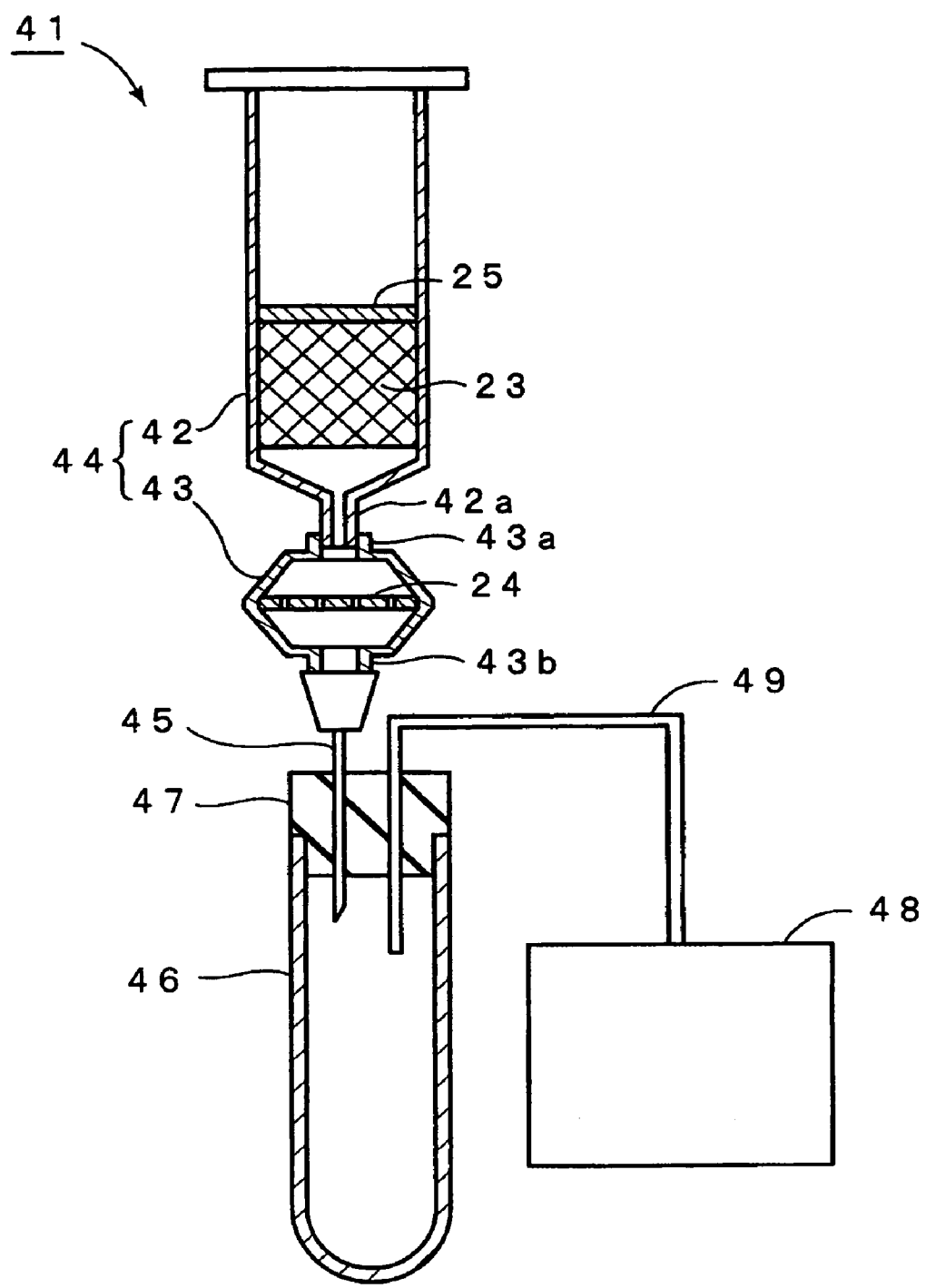
FIG. 7 is a schematic front section view of a blood testing system using a filter apparatus according to a further embodiment of the present invention.

In the first and the second embodiments, the first and the second filter members are serially connected in such a manner that the first and the second filter members directly contact with each other. However, the first filter member and the second filter member are not necessarily connected directly insofar as they are connected serially from upstream side to the downstream side. FIG. 7 is a schematic front section view of a blood testing system equipped with a filter apparatus of other embodiment of the present invention in which the first and the second filter members are disposed at a distance.

In a blood testing system 41, a filter apparatus 44 is made up of a syringe 42 and a filter holder 43. In the syringe 42, the first filter member 23 and the third filter member 25 are accommodated so that the third filter member 25 is on the upstream side. To a tip end 42a of the syringe 42, an inlet port 43a of the filter holder 43 is connected in a liquid-tight manner. In the filter holder 43, the second filter member 24 is provided. Corpuscles in the blood having moved into the filter holder 43 are captured by the second filter member 24. Consequently, separated plasma or serum is collected via an outlet port 43b of the filter holder 43.

In the blood testing system 41, an injection needle 45 is attached to the outlet port 43b of the filter holder 43. And the needle end of the injection needle 45 pierces a plug member 47 attached to a plasma or serum storage container 46. The plug member 47 is made of an elastic material and attached so as to hermetically seal the upper end opening of the storage container 46.

Figure 8:
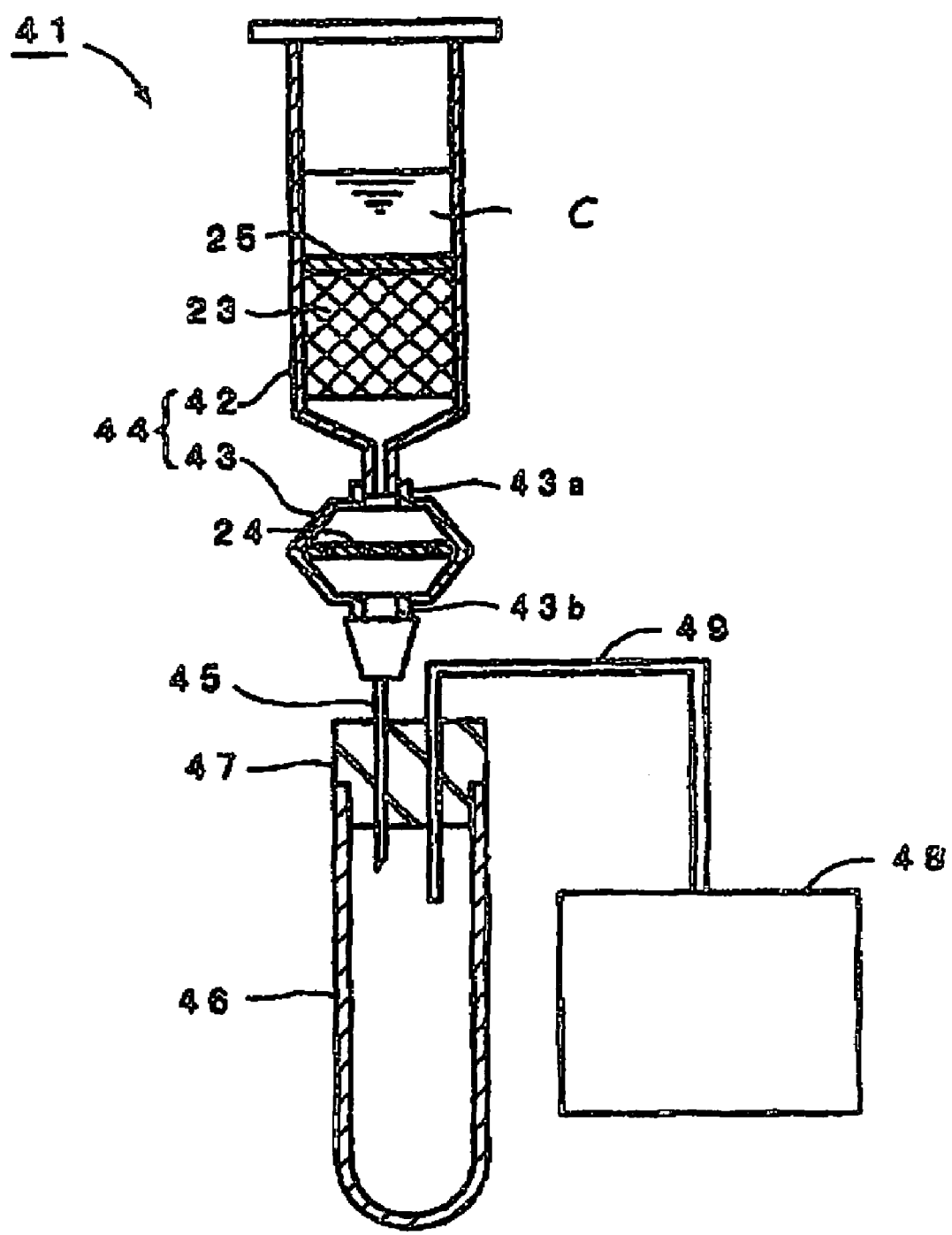
FIG. 8 is a schematic front section view for explaining a plasma separating method using the blood testing system shown in FIG. 7.

On the other hand, fitted into the plug member 47 is a flow channel 49 connected to a constant pressure suction pump 48. As shown in FIG. 8, by driving the constant pressure suction pump 48 after blood collected in a first internal space C is supplied into the syringe 42, the internal space of the storage container 46 is depressurized to cause suctioning of the blood. The suctioned blood sequentially passes through the third filter member 25, the first filtering member 23 and the second filter member 24, and separated plasma or serum is finally collected into the storage container 45.

Accordingly, by removing the injection needle 45 and the flow channel 49 from the storage container 46, it is possible to obtain separated plasma or serum within the storage container 46.

Figure 9:
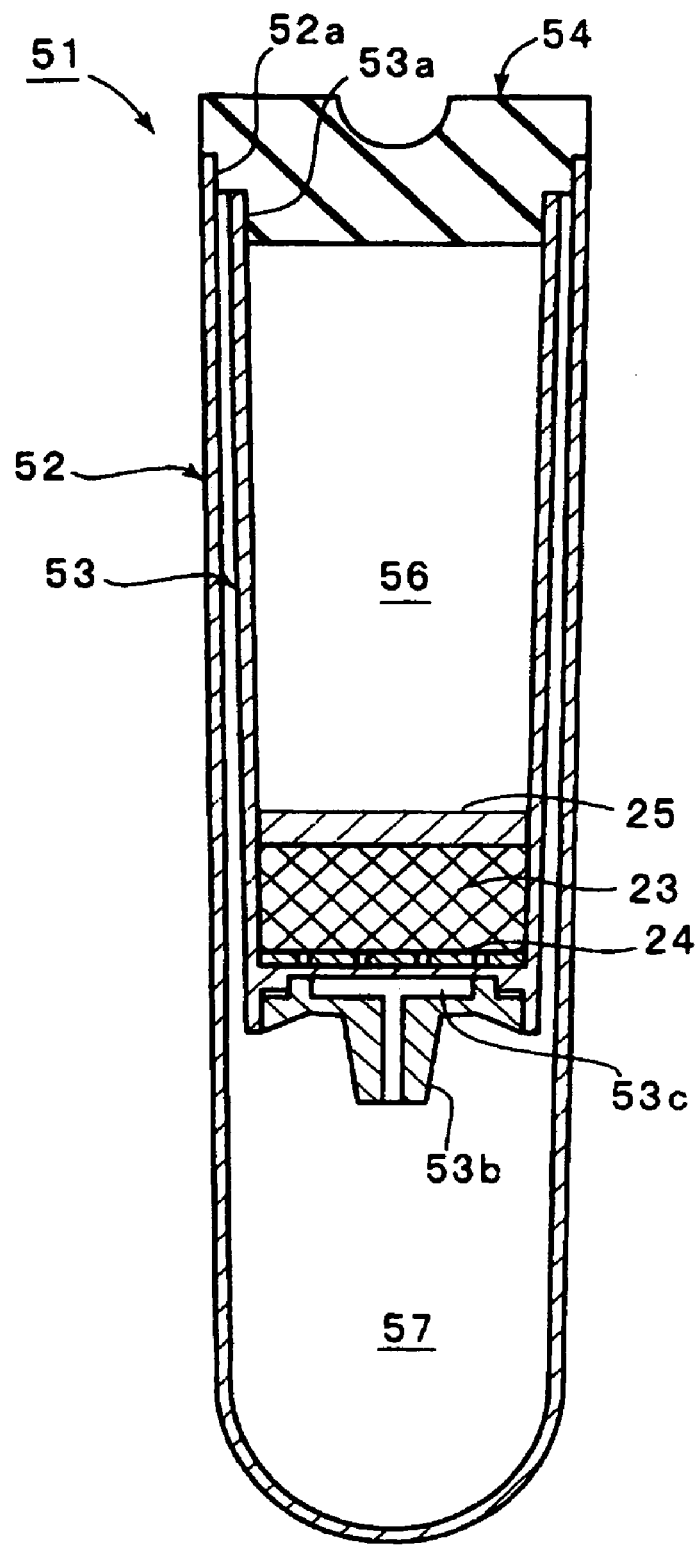
FIG. 9 is a schematic front section view of a blood testing container according to the present invention.

FIG. 9 is a schematic front section view of one embodiment of a blood testing container according to the present invention. A blood testing container 51 has an outer tube 52 and a cylindrical member 53 inserted into the outer tube 52. The outer tube 52 is formed of a cylindrical container having a bottom and an opening 52a at its upper end. The cylindrical member 53 has a cylindrical shape and has an opening 53a at its upper end. At a lower end of the cylindrical member 53 is provided a downward projection 53b which detachably fixed to the cylindrical member 53. In the cylindrical member 53, the third filter member 25, the first filter member 23 and the second filter member 24 constituting the blood separating filter of the present invention are sequentially disposed from top down. In this manner, the blood separating filter configured according to the present invention is accommodated in the cylindrical member 53. Additionally, below the second filter member 24 is formed a plasma or serum retaining part 53c for retaining filtrated plasma or serum. The internal space of the blood testing container 51 is depressurized, and the openings 52a and 53a of the outer tuber 52 and the cylindrical member 53 are hermetically sealed by a plug member 54.

Therefore, in the blood testing container 51, blood is introduced into a blood accommodation part 56 extending above the blood separating filter by piercing the plug member 54 with a vacuum blood collection needle or the like. Then by inserting a blood collection needle into the plug member 54 or by forming a through hole penetrating the plug member 54 after removing the vacuum blood collection needle to allow communication between the internal space of the cylindrical member 53 and the atmosphere, filtration of the collected blood through the blood separating filter proceeds. Then plasma or serum obtained by filtration flows down to a plasma or serum storage part 57 provided below via the plasma or serum retaining part 53c.

The blood testing container according to the present invention is not limited to the structure shown in FIG. 9 as to its concrete structure insofar as the aforementioned blood separating filter is provided. A variety of other structures can be adopted. For example, the first to the third filter members 23 to 25 may be disposed in the storage container in which separated plasma or serum is stored, or the container accommodating the first to the third filter members may be inserted into a container storing separated plasma or serum to form a double-structured blood testing container.

Figure 10:
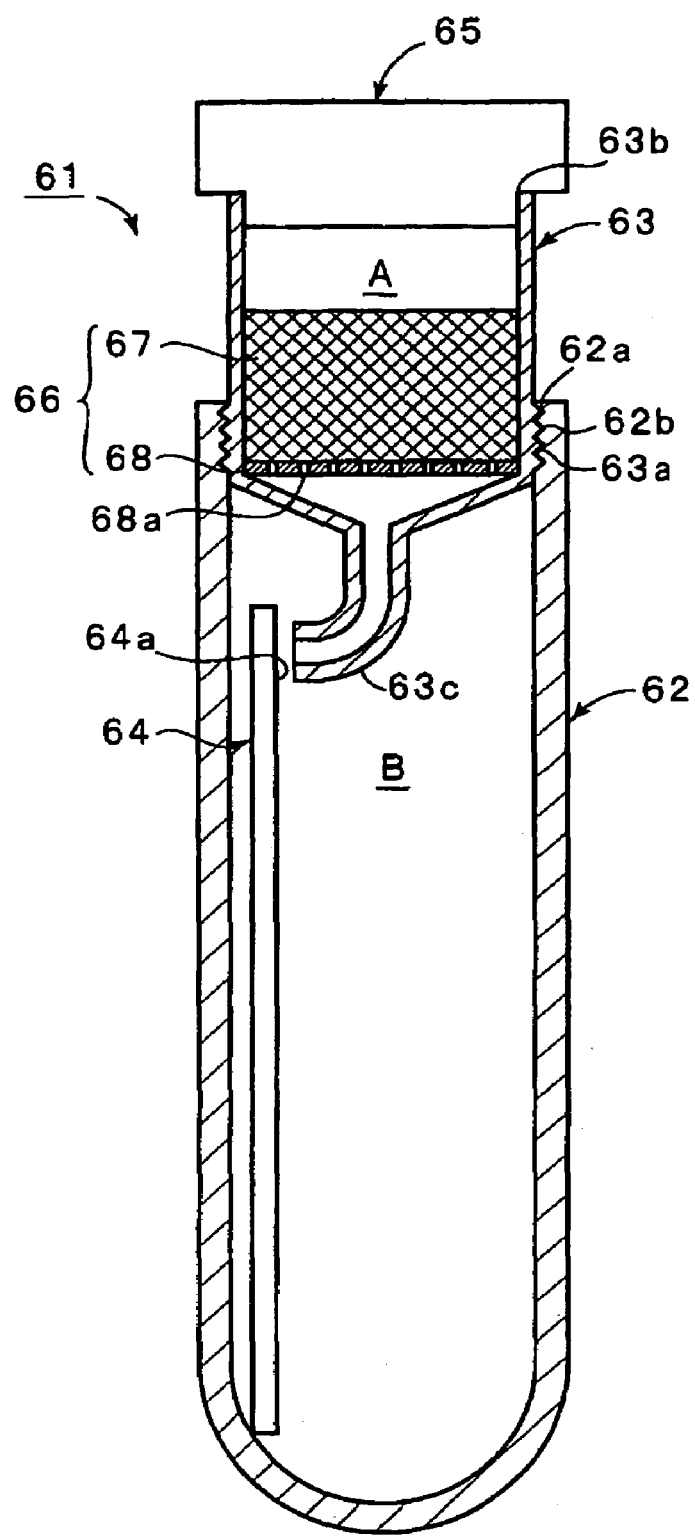
FIG. 10 is a longitudinal section view showing a blood testing container according to other embodiment of the present invention.

FIG. 10 is a longitudinal section view of a blood testing container according to one embodiment of the present invention. A blood testing container 61 is configured by using a blood collection container having a container body 62 and a cylindrical member 63. The container body 62 is formed of a tubular container having a bottom and an opening 62a at its upper end.

In the vicinity of the opening 62a at the upper end of the container body 62 is provided a female screw 62b on the inner periphery.

The cylindrical member 63 is hermetically fixed to the container body 62 by being screwed into the opening 62a of the container body 62. For achieving this fixation, a male screw 63a which meshes with the female screw 62b is formed on the outer periphery in the lower part of the cylindrical member 63.

The cylindrical member 63 has an opening 63b at its upper end. Below the cylindrical member 63 is formed a plasma or serum dropping part 63c so as to project downward. The plasma or serum dropping part 63c is bent so that its tip end is directed to the inner wall of the container body 62. The tip end of the plasma or serum dropping part 63c is located near a specimen supplying part 64a of a blood testing agent strip 64 placed inside the container body 62.

The container body 62 and the cylindrical member 63 can be made of synthetic resins, glass and the like without being particularly limited thereto. However, in order to facilitate that the test result is checked by eyes from outside, preferably, at least the container body 62 is made of a transparent material, and in order to check the blood separation process by eyes, preferably, the cylindrical member 63 is also formed of a transparent material.

For hermetically sealing the opening 63b of the cylindrical member 63, a plug member 65 is attached to the opening 63b.

The plug member 65 is formed of an elastic material such as rubber or elastomer. As the elastic material, any elastic material can be used insofar as it hermetically seals the opening 63b and keeps the reduced pressure in the blood collection container formed of the container body 62 and the cylindrical member 63.

In the cylindrical member 63, a filter apparatus 66 is disposed. The filter apparatus 66 has such a structure that the aforementioned first filter member 67 and the second filter member 68 are serially connected.

In the present embodiment, a blood collection container is made up of the above container body 62 and the cylindrical member 63. The internal space of the blood collection container is depressurized. The degree of depressurization is such that the plug member 65 is pierced with a vacuum blood collection needle and the blood is collected by the pressure difference between inside and outside. Concretely, the degree of depressurization is about 1 to 90 kPa.

In the present embodiment, the blood collection container made up of the container body 62 and the cylindrical member 63 has a first internal space A and a second internal space B in the container. Specifically, a filter 66 consisting of the first filter member 67 and the second filter member 68 is disposed at the boundary between the first internal space A and the second internal space B. In the second space B, a blood testing agent strip 64 is disposed. In the present invention, the blood testing agent strip 64 is disposed so that it extends in the vertical direction and a specimen supplying part 64a is on the side of its upper end in the container body 62.

As the aforementioned blood testing agent strip 64, blood testing agent strips used in detection of components in plasma or serum or substances contained in plasma or serum can be appropriately used.

In the present embodiment, a strip of immunochromatographical diagnostic agent is used as the above blood testing agent strip. Therefore, a specific component in plasma or serum can be detected using the blood testing agent strip 64 by immunochromatography.

In the present embodiment, the blood testing agent strip 64 is used, however, a blood testing agent of other embodiment may be disposed in the second space B in place of the blood testing agent strip 64.

Next, a blood testing method using the blood testing container 61 according to the present embodiment will be explained.

In conducting a blood test, the plug member 65 is pierced with a vacuum blood collection needle. At this time, since the internal space of the blood testing container 61 is depressurized, blood passes the vacuum blood collection needle and introduced to the first space A of the blood testing container 61. After blood is collected, the blood is supplied to the first filter member 67 where plasma or serum moves faster than corpuscles, and the plasma or serum is quickly introduced to the second filter member 68. In the second filter member 68, plasma or serum passes through the aforementioned through holes 68a, and is supplied to the specimen supplying part 64a of the blood testing agent strip 64 via the plasma or serum dropping part 63c. This filtration of blood rapidly proceeds by the pressure difference between the first internal space A and the second internal space B.

In other words, after collecting blood by means of the vacuum blood collection needle, the plug member is pierced with a blood collection needle or the like to allow communication between the external and the internal space A. This reduces the degree of depressurization to generate a pressure difference between the first internal space A and the second internal space B. Owing to this pressure difference, namely the residual pressure in the second internal space, the filtration proceeds quickly. Then, as the through holes 68a of the second filter member 68 are clogged with erythrocytes, the filtration ends.

Also in the second blood testing container 80, since the internal space is depressurized in advance, after piercing the plug body with a vacuum blood collection needle and collecting blood as is the case of the blood testing container 80, filtration of the blood automatically proceeds upon piercing of the plug member with a conducting jig. The blood then flows into filters 76 comprising a first filter 77 and a second filter 78. Below the cylindrical container 83 is formed a plasma of serum dropping part 83c so as to project downward. Plasma or serum serves as a specimen and is supplied to side 74a the blood testing agent strip 74. Accordingly, it is possible to safely complete the operation from the collection of blood to the blood test as is the case of the blood testing container 61 without requiring a centrifuge separator or a centrifuge operation.

Figure 11:
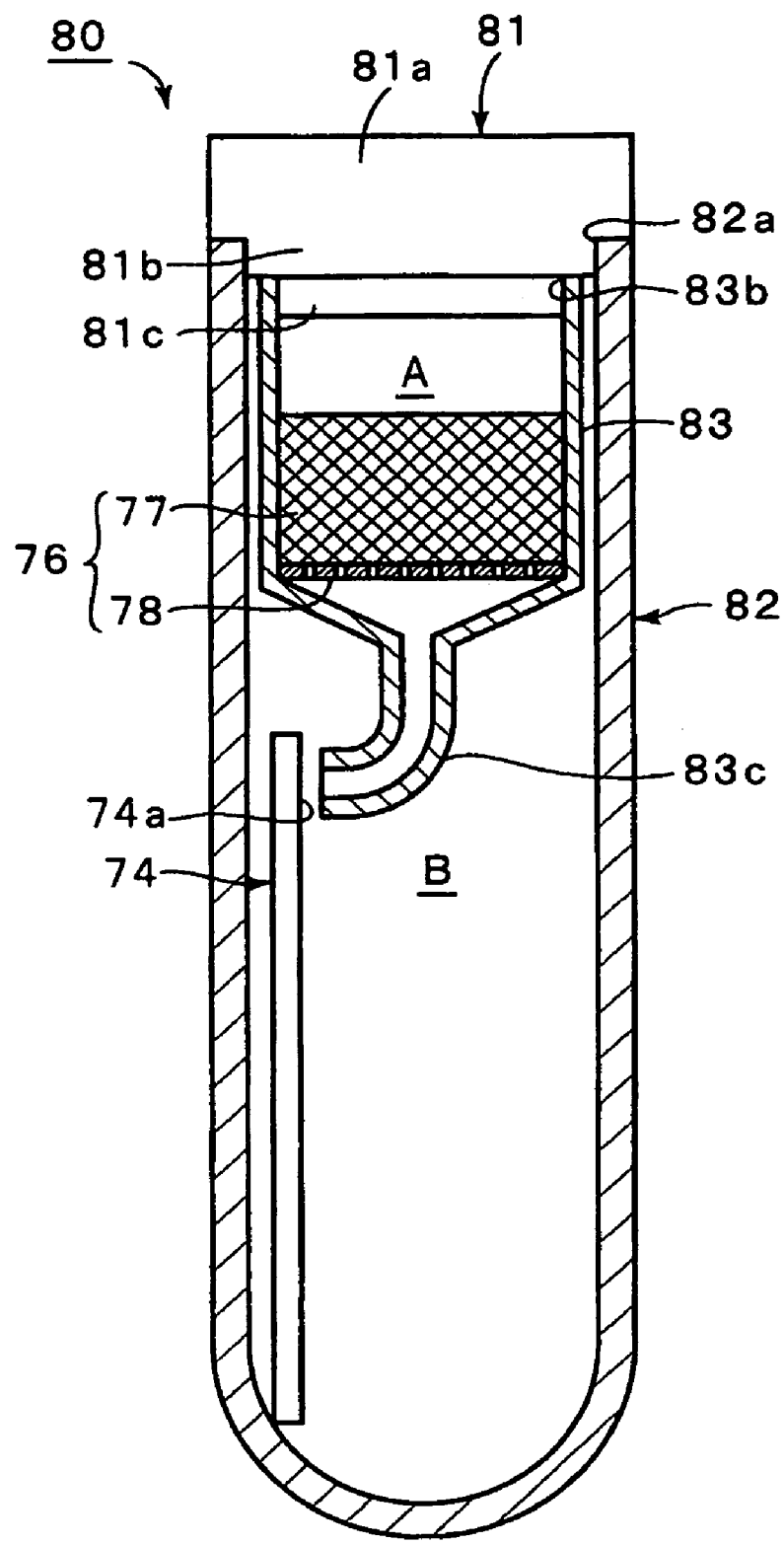
FIG. 11 is a longitudinal section view showing a blood testing container according to a further embodiment of the present invention.

FIG. 11 is a longitudinal section view of a blood testing container according to still another embodiment of the present invention. In the blood testing container 61 illustrated in FIG. 10, the cylindrical member 63 is connected on an upper part of the container body 62, however, in a blood testing container 80 of the present embodiment, a cylindrical member 83 is inserted into a container body 82. A plug member 81 that closes an opening of the cylindrical member 83 closes not only an opening 83b of the cylindrical member 83 but also an opening 82a of the container body 82.

The plug member 81 is configured to have a gripping portion 81a, a larger-diameter portion 81b projecting downward the gripping portion 81a and having a smaller diameter than the gripping portion 81a, and a smaller-diameter portion 81c projecting downward from the bottom surface of the larger-diameter portion 81b and having a smaller diameter than larger-diameter portion 81b. The larger-diameter portion 81b is inserted into the opening 82a and the smaller-diameter portion 81c is pressed into the opening 83b of the cylindrical member 83. In this way, the blood collection container made up of the container body 82 and the 83 is hermetically sealed in such a manner that a certain degree of depressurization is kept in the blood collection container.

Other configuration is as same as that of the blood testing container 61 of the embodiment illustrated in FIG. 10, and hence detailed explanation about each part identical to that shown in FIG. 10 will be omitted by designating the part by the same reference numeral.

Also in the second blood testing container 80, since the internal space is depressurized in advance, after piercing the plug body with a vacuum blood collection needle and collecting blood as is the case of the blood testing container 61, filtration of the blood automatically proceeds upon piercing of the plug member with a conducting jig, and plasma or serum serving as a specimen is supplied the blood testing agent strip 64. Accordingly, it is possible to safely complete the operation from the collection of blood to the blood test as is the case of the blood testing container 61 without requiring a centrifuge separator or a centrifuge operation.

As described above, the blood testing container according to the present invention can be embodied in various forms. When the blood test container includes a blood accommodation part having an opening for the blood test container and accommodating collected blood, a filter accommodation part accommodating the aforementioned first and second filter members or the first to third filter members, and a plasma or serum storage part located subsequent to the filter accommodation part and storing plasma or serum, a volume ratio of the blood accommodation part, filter accommodation part and plasma or serum storage part is preferably in the range of 0.5-2:1:1-10. The reason of this is as follows: if the proportion of the blood accommodation part is less than 0.5, the amount of blood is insufficient relative to the filter amount, so that no or only a small amount of specimen is obtained after separation. On the other hand, if the volume of the blood accommodation part is more than 2.0 in the above ratio, blood exceeding the blood separation capability of the filter is supplied, so that the burden on a subject may increase.

In the blood testing container according to the present invention, as described above, it is possible to separate blood by using pressure difference. In this case, blood is driven by pressure difference between the blood accommodation part and the plasma or serum storage part, to flow into the filter for achieving separation. As the separation of blood proceeds, the internal pressure of the plasma or serum storage part increases, and hence driving force of filtration decreases. The aforementioned pressure difference depends on the volume of the plasma or serum storage part. If the volume of the plasma or serum storage part is less than 1 in the above ratio, the driving force is insufficient for blood separation, leading the problem that no or only a small amount of specimen is obtained after separation. To the contrary, if the volumetric proportion of the plasma or serum storage part is more than 10, the driving force is sufficient for blood separation, however, such a configuration is not favorable because the size may increase more than necessary, the cost may rise, and the amount of waste after uses may increase.

In the blood testing container according to the present invention, it is preferred that an aqueous solution having an osmotic pressure of 200 to 350 mOsm/kg is added at at least one point in the course from blood accommodation part where the collected blood is supplied to the filter accommodation part. In this case, the collected blood is mingled with the aqueous solution in the process before the end of the blood separation and hence concentration of corpuscles in the blood decreases. That is, the hematocrit value decreases. When the filter apparatus is used for separating blood, the smaller the hematocrit the higher the separation efficiency, and the amount of specimen obtained after separation dramatically increases. However, in a clinical test, the test value does not always change in correspondence with the dilution rate when plasma or serum is diluted. Therefore, dilution should be conducted with care.

In the present invention, designating the amount of collected blood as 1, the amount of the above aqueous solution to be added is preferably in the range of 0.2 to 5. If the proportion of the aqueous solution to be added is less than 0.2, almost no increase in the amount of obtained specimen is expected, whereas if the proportion of the adding amount of the aqueous solution is larger than 5, the blood is diluted in excess so that abnormality occurs in the clinical test value. More preferably, the adding amount of the above aqueous solution is in the range of 0.5 to 3, when the amount of collecting blood is designated as 1.

The aqueous solution to be added is preferably has an osmotic pressure which is equal to that of the blood so that corpuscles, in particular, erythrocytes will not break when the aqueous solution is mingled with the blood. Therefore, the osmotic pressure of the above aqueous solution is preferably in the range of 200 to 350 mOsm/kg. If it is less than 200 mOsm/kg, erythrocytes can expand and collapse, while if it is more than 350 mOsm/kg, contents of the erythrocytes may solve out to give abnormality on the clinical test value. More preferably, the osmotic pressure of the above aqueous solution is in the range of 250 to 300 mOsm/kg.

The solute in the above aqueous solution is not particularly limited, however, solutes whose aqueous solution is strongly acidic or alkaline or reactive with components of the blood are unfavorable. In order to stabilize pH, a combination of inorganic substances having buffer effect is preferably used. Examples of such a combination include, but not limited to, citric acid and disodium hydrogenphosphate; imidazole and hydrochloric acid; trimethylpyridine and hydrochloric acid; triethanol amine and hydrochloric acid; tris(hydroxymethyl) aminomethane and hydrochloric acid; and the like. However, such a combination is not particularly limited insofar as it has a buffer effect at pH of 6 to 8. Also salts such as sodium chloride that will not influence on pH can be preferably used.

Also an internal standard substance may be added to the aqueous solution so that the volume ratio of the collected blood and the aqueous solution is clearer when they are mingled. Such an internal standard substance is also useful for accurately calculating a dilution rate of a plasma or serum obtained through separation of blood. With the internal standard substance, a clinical test value can be calculated accurately. The internal standard substance is not particularly limited, however, it should be a component that does not exist in blood, it should be water soluble, it should have a certain characteristic such as ultraviolet absorption, infrared absorption, near-infrared absorption, fluorescent wavelength, and the concentration thereof in plasma or serum should be measurable by a common measurement method. Examples of such internal standard substance include benzotriazole-based compounds, benzoic acid-based compounds such as methyl p-dimethylbenzoate and octyl p-dimethylaminobenzoate, substances having ultraviolet visible absorption such as oxobenzene, benzoic acid and salicylic acid, and water-soluble metal complexes such as $[Co(H_2O)_6]^{2+}$, $[Co(NH_3)_5]^{2+}$ and $[Fe(\eta\text{-}C_5H_5)_2]$. Also pigments such as indigo, eosin, β-carotene, malachite green, methyl blue and the like can be used. Examples of the fluorescent substances include erhythrosin, rhodamine sulphate, rhodamine B, pinacyanol. Not limited to the internal standard substances recited above, any substance can be used without causing problems insofar as it does not exist in a living body and will not be complicated with the substance to be measured.

In the filter apparatus according to the present invention, preferably an anticoagulant component is added to at least a part of the filter apparatus. In this case, the anticoagulant component is added so as to prevent blood from coagulating. The anticoagulant component is added to the part where the filter member is accommodated, for example in the part where the first and the second filter members or the first to the third filter members of the aforementioned filter apparatus are accommodated, or to the blood accommodation part which is on upstream side of the part where the filter member is accommodated. In the case where an anticoagulant component is added to the blood accommodation part, the anticoagulant component is added to a part that accommodates blood to be tested in the filter apparatus or in a blood testing container having the filter apparatus. Therefore, it is possible to prevent the blood to be tested from coagulating immediately. Even in the case where the anticoagulant component is added to the filter accommodation part connecting with the blood accommodation part, coagulation of blood can be effectively prevented in a similar way. Furthermore, when filtration by the filter member is immediately conducted, the anticoagulant components may be added at a later stage than the filter accommodation part.

Any anticoagulant component can be used without being particularly limited insofar as it has an ability to substantially suppress coagulation of blood. Examples of such anticoagulant component include heparin metal salts such as sodium heparin and lithium heparin. As an anticoagulant component having decalcium ability, sodium citrate, ethylene diamine tetraacetate, oxalate, sodium fluoride and the like can be exemplified.

The adding amount of the anticoagulant component is preferably in the range of 0.5 to 50 units with respect to 1 mL of collected blood in the case of a heparin metal salt, although the adding amount differs depending on the kind of the anticoagulant component. In the case of the sodium citrate, ethylene diamine tetraacetate, oxalate, sodium fluoride and the like, the adding amount is preferably about 0.5 to 20 mg with respect to 1 mL of collected blood.

The filter apparatus or blood testing container of the present invention may partly be added with a coagulation promoting agent that promotes coagulation of blood contrarily to the anticoagulant component. By adding the coagulation promoting agent, it is possible to make blood coagulate and to collect serum as a sample. By adding the coagulation promoting agent, fibrinogen that is not completely removed in the process of separating serum from blood in the filter apparatus is prevented from passing the filter and flowing down to the plasma or serum storage part. Therefore, serum from which fibrinogen has been removed can be obtained with reliability, and hence the problem that the specimen coagulates later can be avoided.

As the coagulation promoting agent, adsorptive inorganic substances such as silica, thrombin and snake venom, as well as thrombin-like enzymes such as papain can be exemplified.

In the case of using a coagulation promoting agent of enzyme type such as thrombin, the coagulation promoting agent is preferably added on the downstream side of the filter. If the coagulation promoting agent is added on the upstream side of the filter, coagulation of blood rapidly proceeds and the filter is clogged with the coagulated blood. This may possibly stop the separation of the blood. In contrast to this, when the coagulation promoting agent is added in the vicinity of the downstream side within the filter accommodation part, only the fibrinogen not removed by the filter can be coagulated by the action of the coagulation promoting agent, so that the fibrinogen can be removed securely within the filter member.

The present invention will be better understood from the following explanation of concrete examples of the present invention. It is to be noted that the present invention is not limited to the following examples.

EXAMPLE 1

A separation membrane made of polycarbonate having a thickness of 10 μm (manufactured by Millipore Corporation, product number: GTTP04700, separation membrane having a plurality of through holes with a circular cross section shape of 0.2 μm in pore size) was prepared. The separation membrane was cut into a piece of 13 mm in diameter and the piece was set into a commercially available filter cartridge (manufacture by Millipore Corporation, trade name: Sphinex filter holder Sx0130000).

EXAMPLE 2

An evaluation sample was prepared in the same manner as Example 1 except that the diameter of the through holes was changed to 0.6 μm.

EXAMPLE 3

An evaluation sample was prepared in the same manner as Example 1 except that the diameter of the through holes was changed to 2.0 μm.

EXAMPLE 4

In a 10 mL-syringe having an inner diameter of 14.5 mm (manufactured by JMS Corporation, made of polypropylene), a separation membrane made of polycarbonate having a number of through holes of 0.2 μm in diameter and used in Example 1 was set, and 1.0 g of polyester fiber having mean fiber diameter of 1.8 μm was charged on the separation membrane, followed by compression into a volume of 4.0 cm$^3$, thereby forming a filter member. The syringe thus prepared was used as an evaluation sample.

EXAMPLE 5

An evaluation sample was obtained in the same manner as Example 4 except that the diameter of the through holes was changed to 0.8 μm.

Comparative Example 1

A separation membrane made of polyvinylidene fluoride having a number of continuous air holes of 0.22 μm in pore size (manufactured by Millipore Corporation under the trade name of Durapore, 125 μm thick) was cut to have a diameter of 13 mm, and placed into a filter cartridge in the same manner as Example 1 to obtain an evaluation sample.

Comparative Example 2

An evaluation sample was obtained in the same manner as Comparative example 1 except that the pore size was changed to 0.65 μm.

Comparative Example 3

An evaluation sample was obtained in the same manner as Example 1 except that the pore size was changed to 3.0 μm.

Comparative Example 4

In a 10 mL-syringe having an inner diameter of 14.5 mm (manufactured by JMS Corporation, made of polypropylene), a separation membrane having continuous air holes of 0.22 μm in pore size and used in Comparative example 1 was set, and then a filter member was set on the separation member by charging 1.0 g of polyester fiber having mean fiber diameter of 1.8 μm on the separation membrane and compressing into a volume of 4.0 cm$^3$, whereby an evaluation sample was obtained.

Comparative Example 5

An evaluation sample was obtained in the same manner as Example 4 except that the separation membrane having through holes of 3.0 μm in pore size used in Comparative example 3 was used.

Test Example 1

Each evaluation sample of Examples 1 to 3 and Comparative example 1 to 3 was used. Using 100 μL of a diluted blood having hematocrit of 10%, filtration was conducted by applying the pressures shown in Table 1 below. The state of obtained plasma was compared with that of the plasma obtained by centrifugal separation (10 min. at 3,000 rpm) of the above diluted blood to determine whether or not hemolysis occurs.

Results are shown in Table 1 below.

TABLE 1

|  | Shape of Hole | Pore Size | Filtration Pressure | Separation State of Plasma |
|---|---|---|---|---|
| Ex. 1 | Through Hole | 0.2 μm | 60 kPa | Hemolysis Not Observed |
| Ex. 2 | Through Hole | 0.6 μm | 60 kPa | Hemolysis Not Observed |
| Ex. 3 | Through Hole | 2.0 μm | 20 kPa | Hemolysis Not Observed |
| Comp. Ex. 1 | Continuous Air Hole | 0.22 μm | 60 kPa | Hemolysis Observed |
|  | Continuous Air Hole | 0.22 μm | 20 kPa | Hemolysis Observed |
| Comp. Ex. 2 | Continuous Air Hole | 0.65 μm | 20 kPa | Hemolysis Observed |
| Comp. Ex. 3 | Through Hole | 3.0 μm | 20 kPa | Erythrocytes Leaked Out |

Test Example 2

Using the evaluation examples of Examples 4, 5 and Comparative examples 4, 5, 4 mL of human blood having a hematocrit of 46.7% was supplied and filtration was conducted by the pressures as shown in Table 2 below. The plasma thus obtained was compared with the plasma obtained by centrifugal separation (10 min. at 3,000 rpm) of the same blood, and presence/absence of hemolysis was checked by eyes. Results are shown in Table 2 below.

TABLE 2

|  | Shape of Hole | Pore Size | Filtration Pressure | Separation State of Plasma |
|---|---|---|---|---|
| Ex. 4 | Through Hole | 0.2 μm | 60 kPa | Hemolysis Not Observed |
| Ex. 5 | Through Hole | 0.8 μm | 60 kPa | Hemolysis Not Observed |
| Comp. Ex. 4 | Continuous Air Hole | 0.65 μm | 20 kPa | Hemolysis Observed |
| Comp. Ex. 5 | Through Hole | 3.0 μm | 20 kPa | Erythrocytes Leaked Out |

EXAMPLE 6

A corpuscles blocking membrane made of polycarbonate having through holes of 0.2 μm in pore size and having a porosity of 14% was prepared. The corpuscles blocking membrane is available from Millipore Corporation under the trade name of Isopore GTTP and has a thickness of 10 μm. The corpuscles blocking membrane was cut to have a diameter of 13 mm and set into a commercially available filter holder (manufactured by Millipore Corporation under the trade name of Sphinex filter holder, effective filtration area: about 0.7 cm$^2$) to thereby obtain a sample for evaluation.

EXAMPLE 7

An evaluation sample was obtained in the same manner as Example 6 except that the pore size and the porosity were changed to 0.8 μm and 15%, respectively. Isopore ATTP (trade name) manufactured by Millipore Corporation was used as the corpuscles blocking membrane.

EXAMPLE 8

An evaluation sample was obtained in the same manner as Example 6 except that the pore size and the porosity were changed to 1.2 μm and 23%, respectively. Isopore RTTP (trade name) manufactured by Millipore Corporation was used as the corpuscles blocking membrane.

EXAMPLE 9

An evaluation sample was obtained in the same manner as Example 6 except that the pore size and the porosity were changed to 2.0 μm and 8%, respectively. Isopore TTTP (trade name) manufactured by Millipore Corporation was used as the corpuscles blocking membrane.

EXAMPLE 10

In a 10 mL-syringe having an inner diameter of 14.5 mm, a corpuscles blocking membrane having a pore size of 0.2 μm and porosity of 14% and used in Example 6, cut to have a diameter of 14.5 mm was set, and then a filter member was set by charging 1.0 g of polyester fiber having mean fiber diameter of 1.8 μm and compressing into a volume of 4.0 cm$^3$, whereby an evaluation sample was obtained.

EXAMPLE 11

An evaluation sample was obtained in the same manner as Example 10 except that the pore size and the porosity were changed to 0.8 μm and 16%, respectively.

EXAMPLE 12

An evaluation sample was obtained in the same manner as Example 10 except that the pore size and the porosity were changed to 2.0 μm and 8%, respectively.

Comparative Example 6

An evaluation sample was obtained in the same manner as Example 6 except that a 125 μm-thick polyvinylidene fluoride membrane having a plurality of holes (manufactured by Millipore Corporation under the trade name of Durapore GVWP, 0.22 μm pore size and 70% porosity) was used as the corpuscles blocking membrane.

Comparative Example 7

An evaluation sample was obtained in the same manner as Example 6 except that a 150 μm-thick cellulose-mixed ester film having a plurality of holes (manufactured by Millipore Corporation under the trade name of MF-Millipore DAWP, 0.65 μm pore size and 81% porosity) was used as the corpuscles blocking membrane.

Comparative Example 8

An evaluation sample was obtained in the same manner as Comparative example 6 except that the pore size and the porosity were changed to 5.0 μm and 70%, respectively.

Comparative Example 9

An evaluation sample was obtained in the same manner as Example 6 except that the pore size and the porosity were changed to 3.0 μm and 14%, respectively.

Comparative Example 10

An evaluation sample was obtained in the same manner as Example 10 except that a corpuscles blocking membrane made of polyvinylidene fluoride having a pore size of 0.22 μm, porosity of 70% and thickness of 125 μm, namely, the corpuscles blocking membrane used in Comparative example 6 was used.

Comparative Example 11

An evaluation sample was obtained in the same manner as Example 10 except that a corpuscles blocking membrane made of cellulose-mixed ester having a pore size of 0.65 μm, porosity of 81% and thickness of 150 μm, namely, the corpuscles blocking membrane used in Comparative example 7 was used.

Comparative Example 12

An evaluation sample was obtained in the same manner as Example 10 except that a 9 μm-thick polycarbonate film having a plurality of holes (manufactured by Millipore Corporation under the trade name of Isopore TSTP, 3.0 μm pore size and 14% porosity) was used as a corpuscles blocking membrane.

Test Example 3

Blood obtained from a healthy individual was separated by centrifugation into plasma and corpuscle components. Using the corpuscles blocking membrane of Examples 6 to 9 and Comparative examples 6 to 8, 200 μL of plasma component obtained by the centrifugal separation was applied and filtered at pressures listed in Table 3 below. Before ending of the filtration, another 200 μL of blood not subjected to centrifugal separation was added and filtration was continued. After 10 minutes, the state of plasma having been filtered was compared with that of the centrifuged plasma to determine whether hemolysis occurred. The results are shown in Table 3.

TABLE 3

| | Pore Size | Porosity | Filtration Pressure | Separation State of Plasma |
|---|---|---|---|---|
| Ex. 6 | 0.2 μm | 14% | 60 kPa | Hemolysis Not Observed |
| Ex. 7 | 0.8 μm | 16% | 60 kPa | Hemolysis Not Observed |
| Ex. 8 | 1.2 μm | 23% | 60 kPa | Hemolysis Not Observed |
| Ex. 9 | 2.0 μm | 8% | 60 kPa | Hemolysis Slightly Observed |
| | | | 40 kPa | Hemolysis Not Observed |

TABLE 3-continued

| | Pore Size | Porosity | Filtration Pressure | Separation State of Plasma |
|---|---|---|---|---|
| Comp. Ex. 6 | 0.22 μm | 70% | 20 kPa | Hemolysis Observed |
| Comp. Ex. 7 | 0.65 μm | 81% | 20 kPa | Hemolysis Observed |
| Comp. Ex. 8 | 5.0 μm | 70% | 20 kPa | Erythrocytes Leaked Out |
| Comp. Ex. 9 | 3.0 μm | 14% | 20 kPa | Erythrocytes Leaked Out |

As is apparent from Table 3, in Examples 5 to 9, plasma in which hemolysis did not occur could be obtained even when a pressure of 60 kPa or 40 kPa was applied, while in Compartive examples 6 to 8, hemolysis or leakage of erythrocytes was observed at a pressure of as low as 20 kPa.

Test Example 4

Using filter apparatus incorporating the corpuscles blocking membranes according to Examples 10 to 12 and Comparative examples 10 to 12, 4 mL of human blood having a hematocrit of 46.7% was filtrated at the pressures listed in Table 4 below. After leaving for 10 minutes, the state of the obtained plasma was compared with that of the plasma having subjected to centrifugal separation (3,000 rpm×10 min.) to determine whether hemolysis occurred.

TABLE 4

| | Pore Size | Porosity | Filtration Pressure | Separation State of Plasma |
|---|---|---|---|---|
| Ex. 10 | 0.2 μm | 14% | 60 kPa | Hemolysis Not Observed |
| Ex. 11 | 0.8 μm | 16% | 60 kPa | Hemolysis Not Observed |
| Ex. 12 | 2.0 μm | 8% | 60 kPa | Hemolysis Not Observed |
| Comp. Ex. 10 | 0.22 μm | 70% | 20 kPa | Hemolysis Observed |
| Comp. Ex. 11 | 0.65 μm | 81% | 20 kPa | Hemolysis Observed |
| Comp. Ex. 12 | 3.0 μm | 14% | 20 kPa | Erythrocytes Leaked Out |

In Examples 10 to 12, hemolysis did not occur and filtration automatically stopped after plasma was filtrated. Contrarily, in Comparative examples 10 to 12, hemolyzed plasma was gradually filtrated or erythrocytes were directly filtered.

Next, concrete examples will be explained.

EXAMPLE 13

The blood testing system 41 illustrated in FIG. 7 was constructed. The syringe 42 was charged with 1.0 g of polyethylene terephthalate fiber having mean fiber diameter of 1.8 μm for forming the first filter member, and then with 0.22 g of fiber composed of polyethylene terephthalate having mean fiber diameter of 3.5 μm and bulk density of 0.1 g/cm$^3$ for forming the third filter member. Then these fiber materials were compressed so that the total volume was 4 cm$^3$ to produce the first filter member 23 and the third filter member 25.

As the filter holder 43, Sphinex filter holder (trade name) manufactured by Millipore Corporation was used, and as the second filter, a filter having pore size of 0.4 μm and porosity of 13% (manufactured by Millipore Corporation under the trade name of Isopore HTTP) was punched out to a diameter of 13 mm and set. The above syringe 42 and the filter holder 43 were connected as shown in FIG. 7, thereby constructing a filter apparatus.

EXAMPLE 14

A filter apparatus was formed in the same manner as Example 13 except that 0.02 g of fiber having mean fiber diameter of 6.0 μm and bulk density of 0.1 g/cm³ was used as a material forming the third filter member.

EXAMPLE 15

A filter apparatus was formed in the same manner as Example 13 except that 0.05 g of fiber having mean fiber diameter of 10.0 μm and bulk density of 0.1 g/cm³ was used as a material forming the third filter member.

Comparative Example 13

A filter apparatus was formed in the same manner as Example 13 except that the third filter member was not formed.

Test Example 5

Using each of the filter apparatuses according to Examples 13 to 15 and Comparative example 13, the plasma or serum storage container 46 and the suction pump 48 were connected to each other as shown in FIG. 7 and FIG. 8, and 4 mL of blood having hematocrit of about 40% was added into the syringe 42, after which suction filtration was conducted at a pressure of 50 kPa. The plasma thus obtained was compared with the plasma obtained by subjecting the same blood to centrifugal separation, and presence/absence of hemolysis was observed.

Test Example 6

Using each of the filter apparatuses according to Examples 13 to 15 and Comparative example 13, blood having hematocrit of about 40% was fed into a glass container and left for two minutes for promoting coagulation, after which 4 mL of the blood whose coagulation was promoted was added to each filter apparatus and suction filtration at a pressure of 50 kPa was followed in the same manner as Example 5. The plasma thus obtained was compared with the plasma obtained by subjecting the same blood to centrifugal separation, and presence/absence of hemolysis was observed.

The results are shown in Table 5 below.

Presence/absence of hemolysis was determined in the following manner.

No hemolysis: no difference was observed compared to plasma obtained by centrifugal separation.

Slight hemolysis: plasma was slightly reddish compared to plasma obtained by centrifugal separation.

Weak hemolysis: plasma was apparently reddish compared to plasma obtained by centrifugal separation.

TABLE 5

|  | Result of Test Example 5 | Result of Test Example 6 |
|---|---|---|
| Ex. 13 | No Hemolysis | Slight Hemolysis |
| Ex. 14 | No Hemolysis | No Hemolysis |
| Ex. 15 | No Hemolysis | No Hemolysis |
| Comp. Ex. 13 | No Hemolysis | Weak Hemolysis |

In the following Examples 16 to 21 and Comparative examples 14 and 15, surface roughness of a plasma or serum separation membrane was measured in the following manner.

More specifically, mean surface roughness Ra was measured as a shape of filter surface by AFM and DFM with the use of a scanning-type probe microscope. Herein the mean surface roughness Ra is mean surface roughness Ra along central line based on the standard of JIS B0601, extended three-dimensionally so as to be applicable to the measurement surface, and hence is a mean value of absolute values of deviation from a reference surface to a designated surface. The used apparatus was SPI3800N and SPA400 manufactured by SII Corporation. Used probes are as follows.

TABLE 6

|  | Deep Needle End Diameter | Material | Length of Cantilever | Spring Constant |
|---|---|---|---|---|
| AFM | 10 nm | Silicon Nitride | 100 μm | 0.09 N/m |
| DFM | 10 nm | Silicon | 100 μm | 20.0 N/m |

The scanning frequency in the measurement was 1 Hz, and then number of acquiring data X/Y was 256/256.

EXAMPLE 16

A filter made of polycarbonate having a pore size of 0.4 μm, porosity of 18% and mean surface roughness of 58.62 nm was cut to have a diameter of 13 mm, and set into a commercially available filter cartridge, to obtain an evaluation sample.

EXAMPLE 17

A filter made of polycarbonate having a pore size of 0.4 μm, porosity of 15% and mean surface roughness of 24.63 nm was cut to have a diameter of 13 mm, and set into a commercially available filter cartridge, to obtain an evaluation sample.

EXAMPLE 18

A filter made of polycarbonate having a pore size of 0.4 μm, porosity of 15% and mean surface roughness of 27.53 nm was cut to have a diameter of 13 mm, and set into a commercially available filter cartridge, to obtain an evaluation sample.

EXAMPLE 19

A commercially available 10 mL-plastic syringe was charged with 1.0 g of polyester fiber having fiber diameter of 1.8 μm with compression to achieve a volume of 4 mL, and the filter sample according to Example 16 was set on the downstream side, to obtain an evaluation sample.

EXAMPLE 20

A commercially available 10 mL-plastic syringe was charged with 1.0 g of polyester fiber having fiber diameter of 1.8 μm with compression to achieve a volume of 4 mL, and the filter sample according to Example 17 was set on the downstream side, to obtain an evaluation sample.

EXAMPLE 21

A commercially available 10 mL-plastic syringe was charged with 1.0 g of polyester fiber having fiber diameter of 1.8 μm with compression to achieve a volume of 4 mL, and the filter sample according to Example 18 was set on the downstream side, to obtain an evaluation sample.

Comparative Example 14

A filter made of polyvinylidene difluoride having a pore size of 0.45 μm, porosity of 70% and mean surface roughness of 147.70 nm was cut to have a diameter of 13 mm, and set into a commercially available filter cartridge, to obtain an evaluation sample.

Comparative Example 15

A commercially available 10 mL-plastic syringe was charged with 1.0 g of polyester fiber having fiber diameter of 1.8 μm with compression to achieve a volume of 4 mL, and the filter sample according to Comparative example 14 was set on the downstream side, to obtain an evaluation sample.

Test Example 7

Using each of the separation membranes according to Examples 16 to 18 and Comparative example 14, 500 μL of blood having hematocrit of 10% was developed on each of the separation membranes, after which filtration was conducted at respective pressures shown in Tables 7 and 8 below. The plasma thus obtained was compared with the plasma obtained by subjecting the same blood to centrifugal separation, and checked for hemolysis.

TABLE 7

|  | Mean Surface Roughness | Pore Size | Filtration Pressure | Separation State of Plasma |
|---|---|---|---|---|
| Ex. 16 | 58.62 nm | 0.4 μm | 60 kPa | No Hemolysis |
| Ex. 17 | 24.63 nm | 0.4 μm | 60 kPa | No Hemolysis |
| Ex. 18 | 27.53 nm | 0.4 μm | 60 kPa | No Hemolysis |
| Comp. Ex. 14 | 147.70 nm | 0.45 μm | 60 kPa | Hemolysis |

Test Example 8

Using each of the separation filters according to Examples 19 to 21 and Comparative example 15, 4 mL of blood collected from a healthy volunteer was developed on each of the separation filters, after which filtration was conducted at respective pressures shown in Table 8. The plasma thus obtained was compared with the plasma obtained by subjecting the same blood to centrifugal separation, and checked for hemolysis.

TABLE 8

|  | Mean Surface Roughness | Pore Size | Filtration Pressure | Separation State of Blood | Amount of Specimen | Remaining Fibrinogen Amount* |
|---|---|---|---|---|---|---|
| Ex. 19 | 58.62 nm | 0.4 μm | 60 kPa | No Hemolysis | 0.52 mL | Quantification Limit or Less |
| Ex. 20 | 24.63 nm | 0.4 μm | 60 kPa | No Hemolysis | 0.53 mL | Quantification Limit or Less |
| Ex. 21 | 27.53 nm | 0.4 μm | 60 kPa | No Hemolysis | 0.52 mL | Quantification Limit or Less |
| Comp. Ex. 15 | 147.70 nm | 0.45 μm | 60 kPa | Hemolysis | 0.52 mL | Quantification Limit or Less |

*Quantification Limit of Fibrinogen: 10 mg/dL

EXAMPLE 22

To a commercially available 10 mL-plastic syringe, the filter sample of Example 16 was set. Glass fiber having fiber diameter of 1.0 μm and porosity of 90.5%, and then 1.0 g of polyester fiber having fiber diameter of 1.8 μm were placed on the upstream side of the filter sample while compressed to a volume of 4 mL, to thereby obtain an evaluation sample.

EXAMPLE 23

To a commercially available 10 mL-plastic syringe, the filter sample of Example 16 was set. Glass fiber having fiber diameter of 0.6 μm and porosity of 90.4%, and then 1.0 g of polyester fiber having fiber diameter of 1.8 μm were placed on the upstream side of the filter sample while compressed to a volume of 4 mL, to thereby obtain an evaluation sample.

EXAMPLE 24

To a commercially available 10 mL-plastic syringe, the filter sample of Example 16 was set. 0.2 g of fiber having fiber diameter of 1.8 μm was compressed into a volume of 0.4 mL, and then 1.0 g of polyester fiber having fiber diameter of 1.8 μm were placed on the upstream side of the filter sample while compressed to a volume of 4 mL, to thereby obtain an evaluation sample.

TABLE 9

| | Mean Surface Roughness | Pore Size | Filtration Pressure | Separation State of Blood | Amount of Specimen | Remaining Fibrinogen Amount* |
|---|---|---|---|---|---|---|
| Ex. 22 | 58.62 nm | 0.4 μm | 60 kPa | No Hemolysis | 0.74 mL | Quantification Limit or Less |
| Ex. 23 | 58.63 nm | 0.4 μm | 60 kPa | | 0.79 mL | Quantification Limit or Less |
| Ex. 24 | 58.64 nm | 0.4 μm | 60 kPa | | 0.76 mL | Quantification Limit or Less |

*Quantification limit of fibrinogen: 10 mg/dL

INDUSTRIAL APPLICABILITY

In the plasma or serum separation membrane according to the present invention, since a plurality of through holes that penetrate from one side to the other side of the membrane are provided, it is possible to separate plasma or serum from blood readily and securely without causing hemolysis of erythrocytes. In particular, even when a pressure of 60 kPa or less is applied, it is possible to A securely separate plasma or serum without causing breakage of erythrocytes. Therefore, it is possible to improve the efficiency of separation of plasma or serum.

Since the filter apparatus according to the present invention has a filter member through which plasma moves faster provided in the previous stage of the plasma or serum separation membrane configured according to the present invention, plasma dominantly moves quickly toward the plasma or serum separation membrane from blood, so that efficiency of separation is further improved. Additionally, even when a whole blood sample having high hematocrit value is used, plasma can be securely and rapidly separated because the plasma moves quickly through the filter member.

In addition, since the need of centrifugal separation is eliminated, it is possible to rapidly obtain a specimen by using a plasma or serum separation membrane or a filter apparatus of the present invention. Therefore, the present invention is especially useful in emergent cases.

The invention claimed is:

1. A membrane for separating plasma or serum from blood, said membrane being formed from a polymer selected from the group consisting of polycarbonate and polyethylene terephthalate, and having a plurality of through holes provided therein so as to penetrate therethrough and extend from one side to an opposite side thereof, each of said through holes having a diameter of from 0.05 to 2.0 μm, wherein said membrane has a porosity of not more than 30%, and a mean surface roughness of not more than 100 nm.

* * * * *